(12) United States Patent
Wu et al.

(10) Patent No.: US 10,882,845 B2
(45) Date of Patent: Jan. 5, 2021

(54) CRYSTAL FORM OF DEUTERATED AZD9291, PREPARATION METHOD THEREFOR, AND USE THEREOF

(71) Applicant: TYK MEDICINES INC., Zhejiang (CN)

(72) Inventors: Yusheng Wu, Zhejiang (CN); Yang Geng, Zhejiang (CN); Apeng Liang, Zhejiang (CN); Chengshan Niu, Zhejiang (CN)

(73) Assignee: TYK MEDICINES INC., Zhejiang (CN)

( * ) Notice: Subject to any disclaimer, the term of this patent is extended or adjusted under 35 U.S.C. 154(b) by 0 days.

(21) Appl. No.: 16/615,771

(22) PCT Filed: May 22, 2018

(86) PCT No.: PCT/CN2018/087902
§ 371 (c)(1),
(2) Date: Nov. 21, 2019

(87) PCT Pub. No.: WO2018/214886
PCT Pub. Date: Nov. 29, 2018

(65) Prior Publication Data
US 2020/0157080 A1 May 21, 2020

(30) Foreign Application Priority Data

May 24, 2017 (CN) .......................... 2017 1 0374457

(51) Int. Cl.
C07D 401/04 (2006.01)
A61P 35/04 (2006.01)
C07D 403/04 (2006.01)
C07C 309/04 (2006.01)

(52) U.S. Cl.
CPC ............ C07D 403/04 (2013.01); A61P 35/04 (2018.01); C07B 2200/05 (2013.01); C07B 2200/13 (2013.01); C07C 309/04 (2013.01)

(58) Field of Classification Search
CPC .............. C07D 403/04; C07B 2200/13; C07B 2200/05; C07C 309/04
See application file for complete search history.

(56) References Cited

U.S. PATENT DOCUMENTS 8,916,572 B2 12/2014 Wu et al.

FOREIGN PATENT DOCUMENTS

| CN | 102659692 A | 9/2012 |
|----|-------------|--------|
| CN | 103702990 A | 4/2014 |
| CN | 104140418 A | 11/2014 |
| CN | 105153122 A | 12/2015 |
| CN | 105237515 A | 1/2016 |
| CN | 106432231 A | 2/2017 |
| CN | 106674202 A | 5/2017 |
| CN | 107382879 A | 11/2017 |
| WO | 2013014448 A1 | 1/2013 |
| WO | 2017219500 A1 | 12/2017 |
| WO | 2018050052 A1 | 3/2018 |

OTHER PUBLICATIONS

Peter Ballard et al., "Preclinical Comparison of Osimertinib with Other EGFR-TKIs in EGFR-Mutant NSCLC Brain Metastases Models, and Early Evidence of Clinical Brain Metastases Activity", Clinical Cancer Research, vol. 22, No. 20, Oct. 15, 2016, pp. 5130-5140.

Robert Roskoski Jr., "The ErbB/HER receptor protein-tyrosine kinases and cancer", Biochemical and Biophysical Research Communications, vol. 319, 2004, pp. 1-11.

Fortunato Ciardiello et al., "EGFR Antagonists in Cancer Treatment", The New England Journal of Medicine, vol. 358, No. 11, Mar. 13, 2008, pp. 1160-1174.

Thomas J. Lynch et al., "Activating Mutations in the Epidermal Growth Factor Receptor Underlying Responsiveness of Non-Small-Cell Lung Cancer to Gefitinib", The New England Journal of Medicine, vol. 350, No. 21. May 20, 2004, pp. 2129-2139.

J. Guillermo Paez et al, "EGFR Mutations in Lung Cancer: Correlation with Clinical Response to Gefitinib Therapy", Science, vol. 304, Jun. 4, 2004, pp. 1497-1500.

A. John Blacker et al., Crystallisation Process Design, Pharmaceutical Process Development Current Chemical and Engineering Challenges, Royal Society of Chemistry, p. 306-308, (2011).

*Primary Examiner* — Susanna Moore
(74) *Attorney, Agent, or Firm* — Novick, Kim & Lee, PLLC; Bin Lu (57) ABSTRACT

A crystal form of a deuterated AZD9291 has an X-ray powder diffraction measured using Cu-Kα rays with diffraction peaks at 7.1±0.2, 8.5±0.2, 9.4±0.2, 10.3±0.2, 15.1±0.2, 16.3±0.2, 18.7±0.2, 22.0±0.2, 25.6±0.2, and 26.0±0.2. The crystal form of the deuterated AZD9291 is used in the preparation of medicaments for the treatment of cancer. The crystal form of the deuterated AZD9291 provided by the present invention has stable physical and chemical properties and good metabolic stability, and blood concentrations in vivo and concentrations in the brain thereof are significantly improved, achieving an improved therapeutic effect.

9 Claims, 4 Drawing Sheets

CRYSTAL FORM OF DEUTERATED AZD9291, PREPARATION METHOD THEREFOR, AND USE THEREOF

TECHNICAL FIELD

The invention relates to a crystal form of deuterated AZD9291 and a preparation method and use of the crystal form and belongs to the technical field of medicine.

BACKGROUND ART

Epidermal Growth Factor Receptor (EGFR) is a transmembrane protein tyrosine kinase of the erbB receptor family. When bound to a growth factor ligand (e.g., epidermal growth factor (EGF)), the receptor can homodimerize with an additional EGFR molecule, or heterodimerize with another family member (e.g., erbB2 (HER2), erbB3 (HER3), or erbB4 (HER4)). Homodimerization and/or heterodimerization of the erbB receptor results in phosphorylation of key tyrosine residues in the intracellular domain and results in stimulation of many intracellular signaling pathways involved in cell proliferation and survival. Deregulation of erbB family signaling promotes proliferation, invasion, metastasis, angiogenesis, and tumor cell survival, and has been described in many human cancers, including lung cancer, head and neck cancer, and breast cancer.

Therefore, the erbB family represents a reasonable target for the development of anticancer drugs, such as many drugs targeting EGFR or erbB2, which are now widely used in clinical applications, including gefitinib (IRESSA™), Erlotinib (TARCEVA™) and Lapatinib (TYKERB™). Detailed discussion of erbB receptor signaling and its participation in oncogenesis is provided in both New England Journal of Medicine (2008) (No. 358, 1160-1174) and Biochemical and Biophysical Research Communications (2004) (No. 319, 1-11).

Lung cancer is a cancer with the highest incidence in the world, it ranks first among all cancers in China, and it is also the cancer with the highest morbidity and mortality in China. About 30% of lung cancer patients in China have EGFR mutations, wherein L858R and exon 19 deletion mutations account for more than 90%. These patients are more sensitive to EGFR inhibitors. The existing first-generation of EGFR inhibitors, such as erlotinib and gefitinib have good curative effect on such patients, which can reduce tumors in more than 60% of patients and significantly prolong the progression-free survival of patients. However, the vast majority of patients will acquire resistance within 6-12 months. This resistance pattern is a further mutation of EGFR, which reduces its sensitivity to first-generation EGFR inhibitors. The most common of these mutations is the so-called "gatekeeper" mutation T790M (Science, 2004, Vol. 304, 1497-1500; New England Journal of Medicine 2004, 350, 2129-2139). L-threonine (T) originally at this site is replaced by L-methionine (M), and the mutated EGF tyrosine kinase R no longer binds to gefitinib or erlotinib. Thus, the first generation of EGFR inhibitors will no longer work, which results in that no drug is currently available for such patients. Clinically, 50% of patients who develop resistance to first-generation EGFR inhibitors have EGFR T790M mutations. $IC_{50}$ of the first generation of EGFR inhibitors, such as gefitinib and erlotinib, was greater than 3 uM and essentially inactive in the T790M mutant cell line H1975.

In order to increase the inhibitory activity against mutations such as the resistant EGFR T790M, WO2013014448 discloses pyrimidine derivatives which are useful as EGFR inhibitors and their use for the treatment of cancer, wherein G is selected from 4,5,6,7-tetrahydropyrazole[1,5-a]pyridin-3-yl 1H-indol-3-yl, 1-methyl-1H-indol-3-yl or pyrazolo[1,5-a]pyridine-3-yl, $R^2$ is methyl or methoxy, and the structure of which is as follows:

In this patent publication, the compound (AZD9291) as shown in Formula III has been approved by the US FDA on Nov. 13, 2015 and marketed (trade name: Tagrisso, AZD9291) for the treatment of the epidermal growth factor receptor EGFR T790M mutation-positive patients with advanced non-small cell lung cancer.

Formula III

At present, some deuterated AZD9291 compounds have been reported in CN104140418B and CN105237515A, but no crystal forms of the pharmaceutically acceptable salt of deuterated AZD9291 have been reported. A crystal form is a solid state of a drug. The study of the drug crystal form is the study of the basic state of the drug. It is impossible to find a crystal form of a drug (solid material) that is more suitable for treating the disease, unless having a full and comprehensive understanding of the crystal form of the chemical drug. The crystal form of a drug can affect physical and chemical properties of the drug, and directly affect the clinical basis of the drug to play a role in the treatment of disease. At the same time, due to the solubility of some drugs, such drugs shall be made into a pharmaceutically acceptable salt, which can greatly improve its solubility and improve the absorption and utilization of drugs. The applicant has been engaged in the research of drugs for lung cancer, started drug research on EGFR targets very early, and has obtained a series of research results6, such as patent applications CN102659692, U.S. Ser. No. 08/916,572, CN107382879, WO2017219500 and WO2018050052. During our research, it was found that the compound of formula III can enter the brain through the blood-brain barrier, and this result was also reported in Clin. Cancer Res. 2016, 22(20), 5130-5140. However, when the compound of Formula III is metabolized in the body to remove the methyl on the indole nitrogen, the compound of the formula IV (AZ5104) is formed, which cannot pass through the blood-brain barrier. Therefore, it has no effect on tumors metastasized to the brain. If the methyl on the indole nitrogen of the compound of formula III is deuterated, the metabolic stability of the methyl is increased, and the blood concentration and brain concentration in the body are improved, thereby achieving better efficacy. Therefore, it is important to study the stable crystal form of the deuterated AZD9291.

Formula IV

SUMMARY OF THE INVENTION

The present invention primarily provides a crystal form of deuterated AZD9291 and a preparation method and pharmaceutical use thereof.

A crystal form of the deuterated AZD9291 having a structural formula as shown in formula (I) or formula (II) is provided in the present invention.

Formula (I)

Formula (II)

The X-ray powder diffraction of the crystal form obtained by Cu-Kα ray measurement has diffraction peaks at a 2θ angle (the unit of 2θ angle is °) of: 7.1±0.2, 8.5±0.2, 9.4±0.2, 10.3±0.2, 15.1±0.2, 16.3±0.2, 18.7±0.2, 22.0±0.2, 25.6±0.2, and 26.0±0.2.

A crystal form of deuterated AZD9291 having the structural formula as shown in formula (I) or formula (II) is provided in the invention, and the X-ray powder diffraction of the crystal form obtained by the Cu-Kα ray measurement has diffraction peaks at an 2θ angle (unit: °) of: 7.1±0.2, 8.5±0.2, 9.4±0.2, 10.3±0.2, 15.1±0.2, 16.3±0.2, 17.0±0.2, 17.3±0.2, 17.7±0.2, 18.7±0.2, 19.4±0.2, 19.7±0.2, 20.2±0.2, 20.7±0.2, 21.6±0.2, 22.0±0.2, 22.8±0.2, 23.5±0.2, 24.2±0.2, 24.8±0.2, 25.6±0.2, and 26.0±0.2.

A crystal form of the deuterated AZD9291 having a structural formula as shown in the formula (I) or the formula (II) is provided in the present invention, and the X-ray powder diffraction of the crystal form obtained by Cu-Kα ray measurement has diffraction peaks at an 2θ angle (unit: °) of: 7.1±0.2, 8.5±0.2, 9.4±0.2, 10.3±0.2, 12.6±0.2, 14.4±0.2, 15.1±0.2, 15.6±0.2, 16.3±0.2, 17.0±0.2, 17.3±0.2, 17.7±0.2, 18.2±0.2, 18.7±0.2, 19.4±0.2, 19.7±0.2, 20.2±0.2, 20.7±0.2, 21.6±0.2, 22.0±0.2, 22.8±0.2, 23.5±0.2, 24.2±0.2, 24.8±0.2, 25.6±0.2, 26.0±0.2, 26.9±0.2, 27.7±0.2, 28.2±0.2, 29.5±0.2, 30.7±0.2, 31.7±0.2, 32.5±0.2, 33.1±0.2, 33.8±0.2, 34.6±0.2, 34.9±0.2, 35.6±0.2, 37.9±0.2, and 38.7±0.2.

Figure 1:
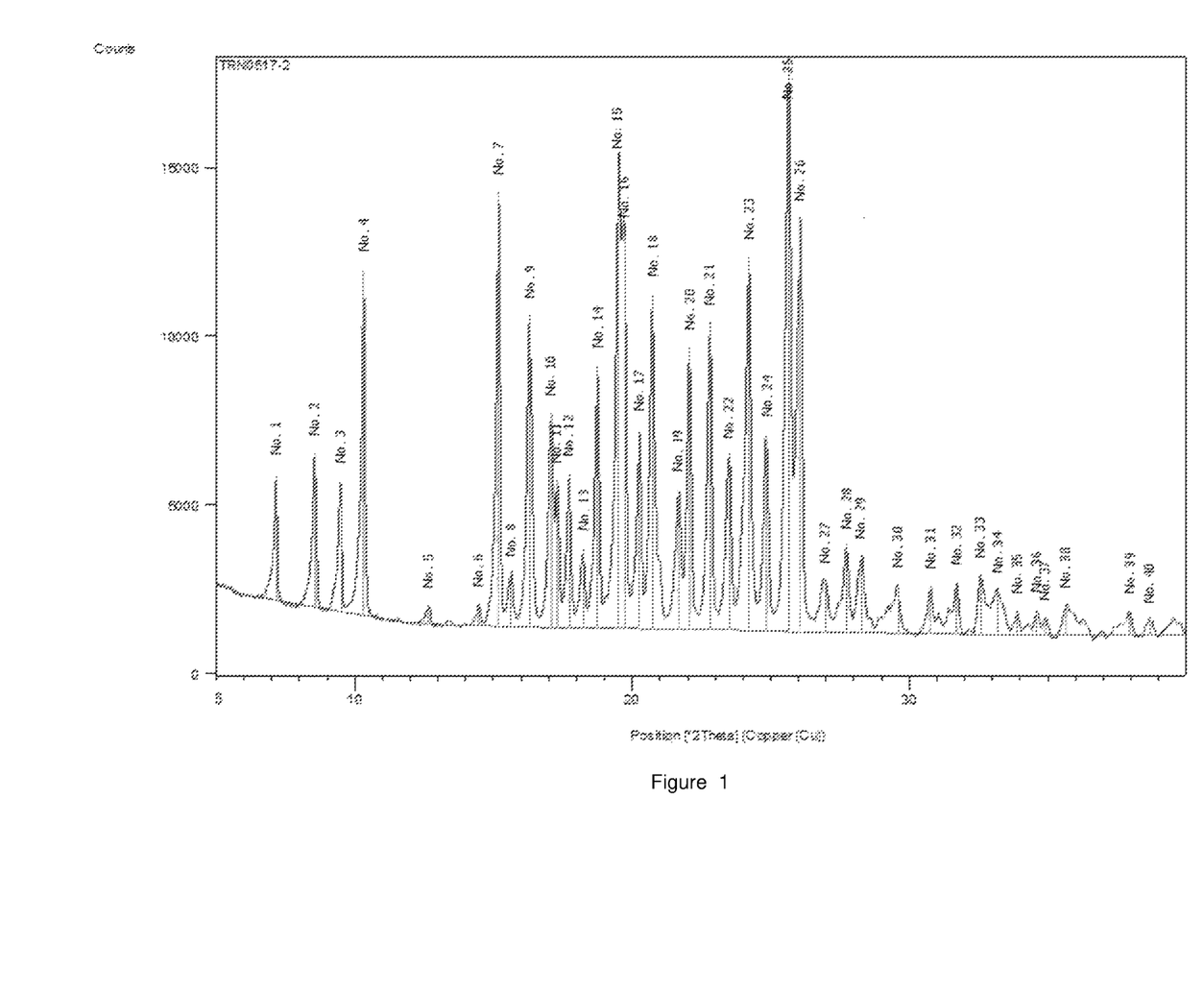
FIG. 1 is an X-ray powder diffraction pattern of the crystal form of deuterated AZD9291 mesylate provided in the present invention.

A crystal form of deuterated AZD9291 having a structural formula as shown in formula (I) or formula (II) is provided in the present invention, and the X-ray powder diffraction pattern of the crystal form obtained by Cu-Kα ray measurement is substantially as shown in FIG. 1.

The invention also provides the use of the crystal form of deuterated AZD9291 in the manufacture of a medicament for the treatment of cancer.

Preferably, the cancer is non-small cell lung cancer.

The preparation method of the crystal form of deuterated AZD9291 is provided in the invention which comprises the following steps:

1) a deuterated AZD9291 compound is added to a solvent system, and heated to 40-80° C., and then methanesulfonic acid is added to the solvent system, wherein the mole number of methanesulfonic acid is 1 to 1.5 times of that of the deuterated AZD9291 compound, maintained at 40 to 80° C. for 1 to 5 hours, and then hot-filtered;

2) the hot-filtered filtrate is allowed to be cooled at room temperature to precipitate crystals;

3) crystals are collected by filtration, and then washed and dried crystals to obtain a crystal form of deuterated AZD9291 mesylate.

As a specific embodiment, the solvent system is any one of methanol, ethanol, isopropanol, acetone, acetonitrile, tetrahydrofuran, water, 1,4-dioxane, t-butyl acetate, an acetone/water mixture, an ethanol/t-butyl acetate mixture, and a 1,4-dioxane/water mixture.

As an optimized embodiment, the solvent system is acetonitrile or an acetone/water mixture.

As an optimized embodiment, the volume ratio of acetone to water in acetone/water mixture is: acetone/water=10:1 to 15:1.

Beneficial effects of the invention are as follows: the crystal form of the deuterated AZD9291 mesylate provided in the invention exhibits stable physical and chemical properties and stable deuteration rate, thereby ensuring the deuteration rate of the deuterated methyl on the indole nitrogen, so that it exhibits good metabolic stability in vivo, and good bioavailability in organisms. For example, in rat experiments, oral bioavailability is 30.9%, and in rat PO (oral) pharmacokinetic experiments, there is a good blood concentration and brain concentration distribution in the body, and the highest blood concentration can reach 117 ng/mL, AUC can reach 1268 h·ng/mL, thereby achieving better efficacy. Moreover, a single impurity is below 0.1%, which is in line with requirements for the development of API and CMC.

DETAILED DESCRIPTION OF THE INVENTION

The technical solution of the present invention will be described in detail below.

Preparation of Crystal Forms of Compounds of Formula (I) or Formula (II)

Formula (I)

Formula (II)

1) Synthesizing Deuterated AZD9291 (D-AZD9291)

The synthetic route is as follows:

intermediate A intermediate B

D-AZD9291

50 mg of intermediate B, 130 mg of intermediate A and 35 mg of p-toluenesulfonic acid monohydrate were dissolved in 5 ml of 2-pentanol, then warmed to 50° C., and stirred under nitrogen overnight. TLC showed that the starting material basically disappeared. The reaction liquid was dried in vacuo, then 20 ml of dichloromethane and 20 ml of saturated aqueous sodium carbonate were added. After being layered, the aqueous layer was washed twice with 20 ml of dichloromethane, and the organic layers were combined, dried, and dried in vacuo. 50 mg of D-AZD9291 product was obtained by column chromatograph. The nuclear magnetic analysis data of D-AZD9291 is as follows: $^1$H-NMR (400 MHz, d$_6$-DMSO) δ 10.22 (s, 1H), 9.16 (s, 1H), 8.68 (s, 1H), 8.33 (d, J=5.2 Hz, 1H), 8.24 (d, J=8.0 Hz, 1H), 7.90 (s, 1H), 7.53 (d, J=8.2 Hz, 1H), 7.26-7.22 (m, 2H), 7.17-7.13 (m, 1H), 7.04 (s, 1H), 6.46-6.40 (m, 1H), 6.30-6.25 (m, 1H), 5.79-5.76 (m, 1H), 3.86 (s, 3H), 2.90-2.37 (m, 2H), 2.72 (s, 3H), 2.30-2.27 (m, 2H), 2.20 (s, 6H);

m/z (ES+) (M+H)$^+$=503.3.

2) Preparing the Crystal Form of the Compound as Shown in Formula (I) or Formula (II)

Method 1: Compound D-AZD9291 (5.02 g, 1 mmol) was added to acetonitrile (40 mL), then the solution was warmed to 70° C., and methanesulfonic acid (0.96 g, 1 mmol) in acetonitrile (10 mL) was added dropwise. After the addition, the mixture was stirred at 70° C. for 2 hours, hot-filtered, and the filtrate was allowed to stand at room temperature for 10 hours, then filtered, and the solid was collected, washed with acetonitrile, and then dried at 40° C. in a vacuum oven to obtain the crystal form. $^1$H-NMR (400 MHz, $d_6$-DMSO) δ9.54 (s, 1H), 9.22 (s, 1H), 8.78 (s, 1H), 8.53 (s, 1H), 8.33-8.30 (m, 2H), 7.94 (s, 1H), 7.53 (d, J=8.2 Hz, 1H), 7.26-7.22 (m, 2H), 7.17-7.13 (m, 1H), 7.01 (s, 1H), 6.72-6.65 (m, 1H), 6.36-6.31 (m, 1H), 5.83-5.80 (m, 1H), 3.89 (s, 3H), 3.30-3.21 (m, 4H), 2.81 (s, 6H), 2.62 (s, 3H), 2.33 (s, 3H); m/z (ES+) (M+H)$^+$=503.3.

Method 2: Compound D-AZD9291 (5.02 g, 1 mmol) was added to acetone (45 mL) and water (4.5 mL), then the solution was warmed to 50° C., and methanesulfonic acid (0.96 g, 1 mmol) in acetone (10 mL) was added dropwise to the above solution. After the addition, the mixture was stirred at 50° C. for 2 hours, hot-filtered, and the filtrate was allowed to stand at room temperature for 10 hours, then filtered, and the solid was collected and washed with a mixture of water and acetone ($V_{acetone}/V_{water}$=10/1), and then dried at 40° C. in a vacuum oven to obtain the crystal form. (400 MHz, $d_6$-DMSO) δ9.54 (s, 1H), 9.22 (s, 1H), 8.78 (s, 1H), 8.53 (s, 1H), 8.33-8.30 (m, 2H), 7.94 (s, 1H), 7.53 (d, J=8.2 Hz, 1H), 7.26-7.22 (m, 2H), 7.17-7.13 (m, 1H), 7.01 (s, 1H), 6.72-6.65 (m, 1H), 6.36-6.31 (m, 1H), 5.83-5.80 (m, 1H), 3.89 (s, 3H), 3.30-3.21 (m, 4H), 2.81 (s, 6H), 2.62 (s, 3H), 2.33 (s, 3H); m/z (ES+) (M+H)$^+$=503.3.

Among them, the synthesis of intermediate A, the route was as follows:

Synthesis of Compound 2: Under a nitrogen atmosphere, compound 1 (15 g, 128.2 mmol) and 260 mL of tetrahydrofuran were added to a 500 mL three-necked flask, and then cooled to 0° C., and sodium hydride (7.7 g, 192.0 mmol) was added in portions. After the addition, the reaction was carried out at 0° C. for 1 hour, and then deuterated methyl iodide (27.8 g, 192.0 mmol) was added dropwise to the reaction mixture, and the reaction mixture was maintained at 0° C. After the addition of deuterated methyl iodide, the temperature was slowly raised to room temperature, the reaction was continued for 10 hours, ice water (200 mL) was added dropwise to the reaction mixture, the reaction mixture was kept at 0° C., and the mixture was extracted with ethyl acetate (100 mL×3). The organic phases were mixed, dried and separated through a column to give 15 g of mixture 2. m/z (ES+) (M+H)$^+$=135.1.

Synthesis of intermediate A: Compound 2 (15 g, 111.9 mmol), Compound 3 (20.0 g, 134.3 mmol), ferric chloride (21.7 g, 134.3 mmol) and 150 mL of DME were added to a 250 mL three-necked flask under a nitrogen atmosphere, then refluxed overnight. After completion of the reaction, the reaction mixture was cooled to room temperature, filtered, and then the filter cake was washed three times with 50 mL of methanol, and then the organic phase was dried in vacuo and separated through a column to give 13.1 g of intermediate A. $^1$H-NMR (400 MHz, d$_6$-DMSO) δ 7.35 (2H, m), 7.64 (1H, dd), 7.88 (1H, d), 8.45-8.52 (1H, m), 8.56 (1H, s), 8.62 (1H, d); m/z (ES+) (M+H)$^+$=247.1.

The synthesis of intermediate B was as follows:

Synthesis of B1-2: 50 g of raw material B1-1 was weighed and completely dissolved in 500 ml of methanol, and 10 g of Pd/C was added thereto, and hydrogenation was carried out at 35° C. for two days. The reaction was monitored by TLC, and the raw material was completely consumed. The Pd/C was directly filtered off, and the methanol phase was dried in vacuo to obtain 39 g of crude product which was directly used in the next step.

Synthesis of B1-3: 39 g of raw material B1-2 was weighed and added to 500 ml of concentrated sulfuric acid in an ice salt bath. The temperature was controlled to be below 10° C., stirred to completely dissolve B1-2. 1 ep of potassium nitrate was added while maintaining the temperature below 10° C., and stirred at room temperature overnight. The next day, the reaction mixture was poured into ice water, pH was adjusted to >7 with ammonia water, the reaction mixture was extracted with ethyl acetate, dried, and separated through a column to obtain 44 g of product. $^1$H-NMR (CDCl$_3$) δ 7.39 (d, J=7.2 Hz, 1H), 6.63 (d, J=12.4 Hz, 1H), 3.94 (s, 3H), 3.90 (broad, 2H).

Synthesis of B1-4: 20 g of raw material B1-3 was weighed and added to 500 ml of dichloromethane, and cooled to −5° C. in an ice salt bath. 1.1 eq of di-tert-butyl dicarbonate in dichloromethane was added dropwise, and then 0.2 eq of DMAP was added. The reaction mixture was allowed to warm to room temperature and stirred overnight. The next day, TLC analysis was conducted, and the reaction was completed. The reaction mixture was separated through a column to obtain 24 g of yellow solid. $^1$H-NMR (CDCl$_3$) δ 8.89 (s, 1H), 6.97 (s, 1H), 6.71 (d, J=12.4 Hz, 1H), 3.97 (s, 3H), 1.53 (s, 9H); m/z (ES+)(M+H)$^+$=285.0.

Synthesis of B1-5: 13.5 g of raw material B1-4 was weighed and added to 200 ml of DMA, and completely dissolved under stirring. Further, 2 eq of N,N,N'-trimethylethylenediamine and 3 eq of DIEA were added, and the mixture was heated to 110° C. and stirred overnight. The next day, the reaction was completed. After treatment, 22 g of oily crude product was obtained, which was directly used in the next step. $^1$H-NMR (CDCl$_3$) δ 8.54 (s, 1H), 6.85 (s, 1H), 6.60 (s, 1H), 3.90 (s, 3H), 3.22 (t, J=6.8 Hz, 2H), 2.81 (s, 3H), 2.55 (t, J=7.2 Hz, 2H), 2.26 (s, 6H), 1.49 (s, 9H); m/z (ES+) (M+H)$^+$=369.3.

Synthesis of B1-6: 22 g of raw material B1-5 was weighed and added to 400 ml of ethyl acetate, completely dissolved under stirring, and then 4.07 g of Pd/C was added thereto, and hydrogenation was carried out at 20° C. overnight. On the next day, the raw material was completely consumed, and Pd/C was directly filtered off and concentrated to give 17 g of black oily crude product which was directly used in the next step. $^1$H-NMR (CDCl$_3$) δ7.517 (s, 1H), 6.941 (s, 1H), 6.61 (s, 1H), 4.10 (m, 2H), 3.76 (s, 3H), 2.92 (m, 2H), 2.62 (s, 3H), 2.40 (m, 2H), 2.27 (s, 6H), 1.49 (s, 9H); m/z (ES+) (M+H)$^+$=339.4.

Synthesis of B1-7: 17.3 g of raw material B1-6 was added to 500 ml of dichloromethane and 1.2 eq of DIEA, and cooled to −5° C. in an ice salt bath under argon. 1.1 eq of acryloyl chloride was added dropwise, and allowed to warm to room temperature. After 3 hours, the reaction was completed. The solvent was directly removed in vacuo at low temperature, to obtain approximately 23 g of crude product. The crude product was directly used in the next step.

Synthesis of intermediate B: 23 g of raw material B1-7 was added to 50 ml of THF, and cooled to −5° C. in an ice salt bath. 100 ml of concentrated hydrochloric acid was added, the reaction temperature was controlled below 10° C., and the reaction mixture was stirred for 2 hours. TLC analysis was conducted, and the reaction was completed. 5.2 g of product was obtained through column chromatograph. $^1$H-NMR (CDCl$_3$) δ10.10 (s, 1H), 7.97 (s, 1H), 6.68 (s, 1H), 6.41-6.21 (m, 2H), 5.65 (m, 1H), 3.81 (s, 3H), 3.76 (s, 2H), 2.82 (m, 2H), 2.65 (s, 3H), 2.20 (s, 6H); m/z (ES+) (M+H)$^+$=293.3.

The X-ray powder diffraction analysis was carried out for the prepared crystal form of the compound of the formula (I) or the formula (II), and the obtained X-ray powder diffraction pattern was shown in FIG. 1. The X-ray powder diffraction peak data were as shown in Table 1. The X-ray powder diffraction patterns of the crystal forms obtained in Method 1 and Method 2 of the present invention are identical.

TABLE 1

| No. | Pos [° 2Th.] | d-spacing [Å] | Rel. Int. [%] | FWHM [° 2Th.] | Area [cts* ° 2Th.] | Backgr. [cts] | Heights [cts] |
| --- | --- | --- | --- | --- | --- | --- | --- |
| 1 | 7.1694 | 12.33032 | 22.11 | 0.1299 | 481.33 | 2165.75 | 3756.61 |
| 2 | 8.5659 | 10.32289 | 26.78 | 0.1299 | 582.81 | 1967.15 | 4548.65 |
| 3 | 9.4876 | 9.3221 | 22.75 | 0.1299 | 495.09 | 1836.81 | 3864.03 |
| 4 | 10.3303 | 8.56344 | 60.37 | 0.0974 | 985.48 | 1716.83 | 10255.21 |
| 5 | 12.6663 | 6.98887 | 3.22 | 0.1299 | 70.08 | 1470.38 | 546.96 |
| 6 | 14.476 | 6.11897 | 3.78 | 0.1299 | 82.21 | 1409 | 641.61 |
| 7 | 15.1897 | 5.83306 | 75.69 | 0.1299 | 1647.5 | 1398.91 | 12858.21 |
| 8 | 15.6284 | 5.67026 | 9 | 0.1299 | 195.82 | 1392.61 | 1528.31 |
| 9 | 16.313 | 5.43381 | 54.22 | 0.1299 | 1180.11 | 1382 | 9210.42 |
| 10 | 17.0853 | 5.18989 | 37.2 | 0.1299 | 809.81 | 1371 | 6320.32 |
| 11 | 17.3199 | 5.12012 | 25.44 | 0.0974 | 415.31 | 1367.36 | 4321.85 |
| 12 | 17.7495 | 4.99717 | 26.91 | 0.1299 | 585.64 | 1361.34 | 4570.75 |
| 13 | 18.2399 | 4.86391 | 13.88 | 0.1299 | 302.12 | 1354.48 | 2357.95 |
| 14 | 18.75 | 4.7327 | 45.91 | 0.1299 | 999.19 | 1347 | 7798.41 |
| 15 | 19.4808 | 4.55679 | 80.55 | 0.1299 | 1753.35 | 1336 | 13684.39 |
| 16 | 19.7309 | 4.49959 | 68.71 | 0.0974 | 1121.69 | 1332.3 | 11672.64 |
| 17 | 20.254 | 4.38453 | 34.89 | 0.1299 | 759.49 | 1325 | 5927.61 |
| 18 | 20.7361 | 4.28369 | 58.51 | 0.1299 | 1273.53 | 1317.84 | 9939.53 |
| 19 | 21.6748 | 4.10024 | 24.69 | 0.1624 | 671.89 | 1304 | 4195.09 |
| 20 | 22.0837 | 4.02524 | 49.32 | 0.1624 | 1341.76 | 1298 | 8377.63 |
| 21 | 22.8189 | 3.89719 | 53.53 | 0.1624 | 1456.39 | 1287.72 | 9093.38 |
| 22 | 23.5089 | 3.78434 | 30.48 | 0.1948 | 995.29 | 1277 | 5178.64 |
| 23 | 24.2191 | 3.67495 | 65.23 | 0.1624 | 1774.84 | 1267 | 11081.66 |
| 24 | 24.8508 | 3.58294 | 34.42 | 0.1624 | 936.45 | 1258 | 5846.99 |
| 25 | 25.6538 | 3.47259 | 100 | 0.1948 | 3264.94 | 1245.82 | 16987.88 |
| 26 | 26.0667 | 3.41852 | 72.22 | 0.1624 | 1964.93 | 1240 | 12268.55 |
| 27 | 26.9869 | 3.304 | 8.92 | 0.2922 | 436.74 | 1227 | 1514.94 |
| 28 | 27.725 | 3.2177 | 15.06 | 0.1624 | 409.67 | 1216 | 2557.88 |
| 29 | 28.2775 | 3.15607 | 13.51 | 0.1948 | 441.06 | 1208 | 2294.87 |
| 30 | 29.592 | 3.0188 | 3.139 | 0.1299 | 182.59 | 1188.47 | 1425.02 |
| 31 | 30.762 | 2.9066 | 8.26 | 0.1299 | 179.69 | 1176 | 1402.42 |
| 32 | 31.7251 | 2.82053 | 8.94 | 0.1299 | 194.63 | 1169 | 1519 |
| 33 | 32.5786 | 2.74856 | 10.21 | 0.1948 | 333.42 | 1164 | 1734.8 |
| 34 | 33.1905 | 2.69928 | 7.67 | 0.3897 | 500.63 | 1159 | 1302.42 |
| 35 | 33.8981 | 2.64453 | 4.01 | 0.1299 | 87.25 | 1155 | 680.93 |
| 36 | 34.6016 | 2.59236 | 4.32 | 0.1624 | 117.6 | 1150 | 734.23 |
| 37 | 34.9163 | 2.56971 | 2.87 | 0.1624 | 76.79 | 1148 | 479.48 |
| 38 | 35.6599 | 2.51781 | 5.14 | 0.1624 | 139.96 | 1143 | 873.91 |
| 39 | 37.9581 | 2.37049 | 4.25 | 0.1624 | 115.72 | 1136 | 722.54 |
| 40 | 38.7101 | 2.32616 | 2.45 | 0.2598 | 106.76 | 1136 | 416.63 |

In Table 1, the 2θ angle value of the X-ray powder diffraction peak has an error range of ±0.2°. It should be understood that the 2θ value of the X-ray powder diffraction pattern may vary slightly between machines and between samples, and the range of values may differ by ±0.2 units, therefore the recited values cannot be construed as absolute values.

Considering that the intensity of the peak represented by the 2θ angle is high or low, especially the intensity of some peaks was lower than 20% of that of the strongest peak, the accuracy of the characterized data is greatly affected by the instrument conditions, and a large error may occur. Therefore, a peak having peak intensity higher than 20% can be selected as the characteristic peak of the crystal form of the present invention.

The melting point of obtained crystal form of the compound of the formula (I) or formula (II) is 239 to 240° C. (melting point test). DSC (differential scanning calorimetry) showed a melting point between 249° C. and 254° C.

The stability of the crystal form of the compound represented by the formula (I) or the formula (II) was further measured, and the apparatus used was a drug accelerated stability test chamber; the accelerated test condition was 40° C., and the relative humidity was 75%. The test results are shown in Table 2.

TABLE 2

| item | month | | | | | |
|---|---|---|---|---|---|---|
| | 0 | 1 | 2 | 3 | 4 | 6 |
| character (visual inspection) | off-white | off-white, no hygroscopicity | off white, no hygroscopicity | off white, no hygroscopicity | off white, no hygroscopicity | off white, no hygroscopicity |
| compound purity and deuteration rate (HPLC & HNMR) | purity 99%, deuteration rate 99% | purity 99%, deuteration rate 99% | purity 99%, deuteration rate 99% | purity 99%, deuteration rate 99% | purity 99%, deuteration rate 99% | purity 99%, deuteration rate 99% |
| crystal form (X-ray powder diffraction) | crystal form of the present invention | | | | | crystal form of the present invention, no crystal form change |

Figure 2:
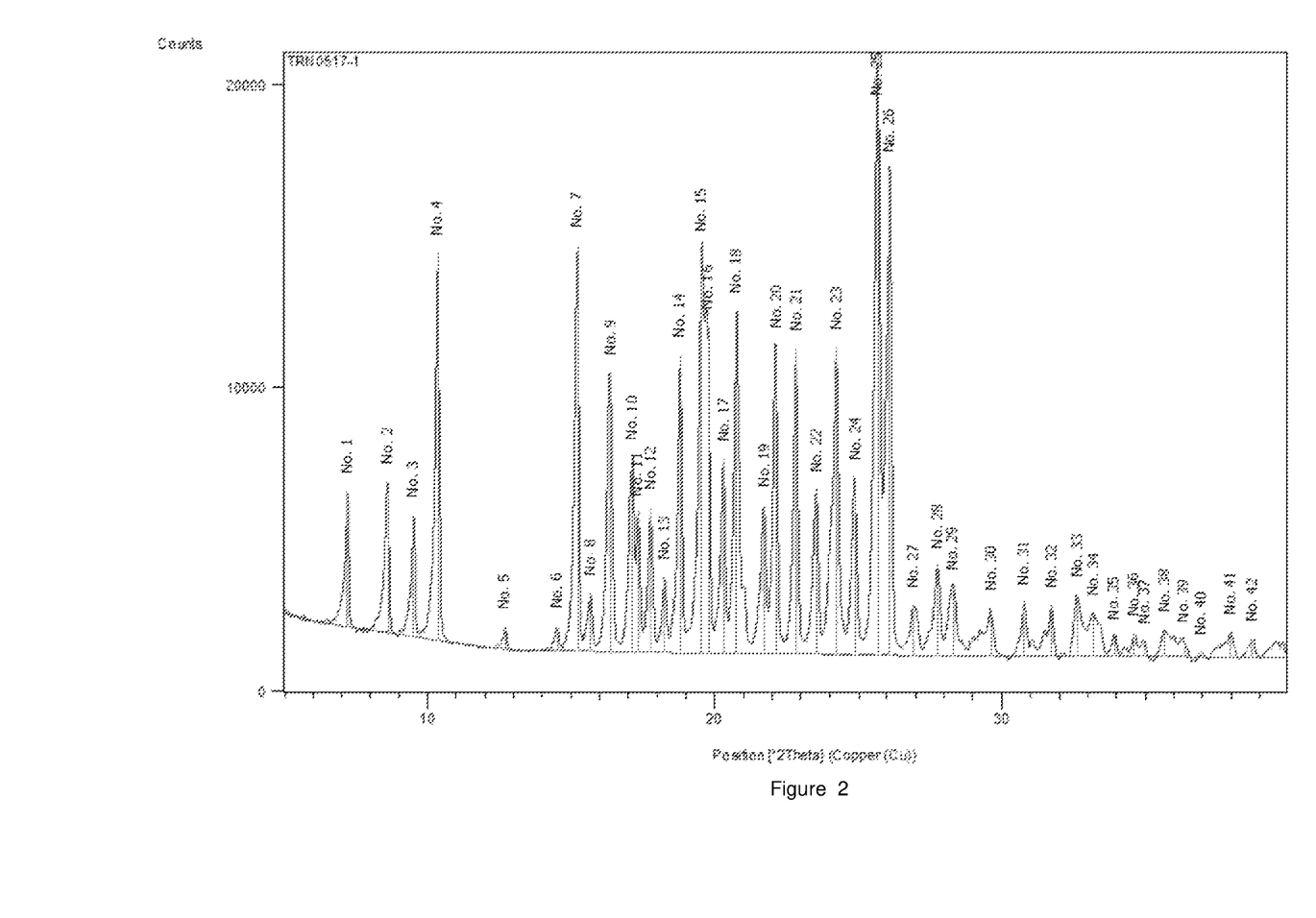
FIG. 2 is an X-ray powder diffraction pattern of the crystal form of deuterated AZD9291 mesylate provided in the present invention after 6-month accelerated stability experiment.

After an accelerated test for six months in the drug accelerated stability test chamber was completed, a sample of the crystal form of the compound of the formula (I) or the formula (II) was obtained and subjected to X-ray powder diffraction analysis, and the obtained X-ray powder diffraction pattern was as shown in FIG. 2.

By comparing FIG. 1 and FIG. 2, it can be concluded that FIG. 1 is consistent with FIG. 2, and the 2θ angle value is consistent within the error range of the instrument, indicating that the crystal form of the present invention is maintained after 6 months of accelerated test.

The above experimental results show that the physicochemical properties of the crystal form are stable and the deuteration rate can be kept unchanged. The deuterated AZD9291 crystal form is suitable for drug applications, such as pharmaceutical preparations.

Figure 3:
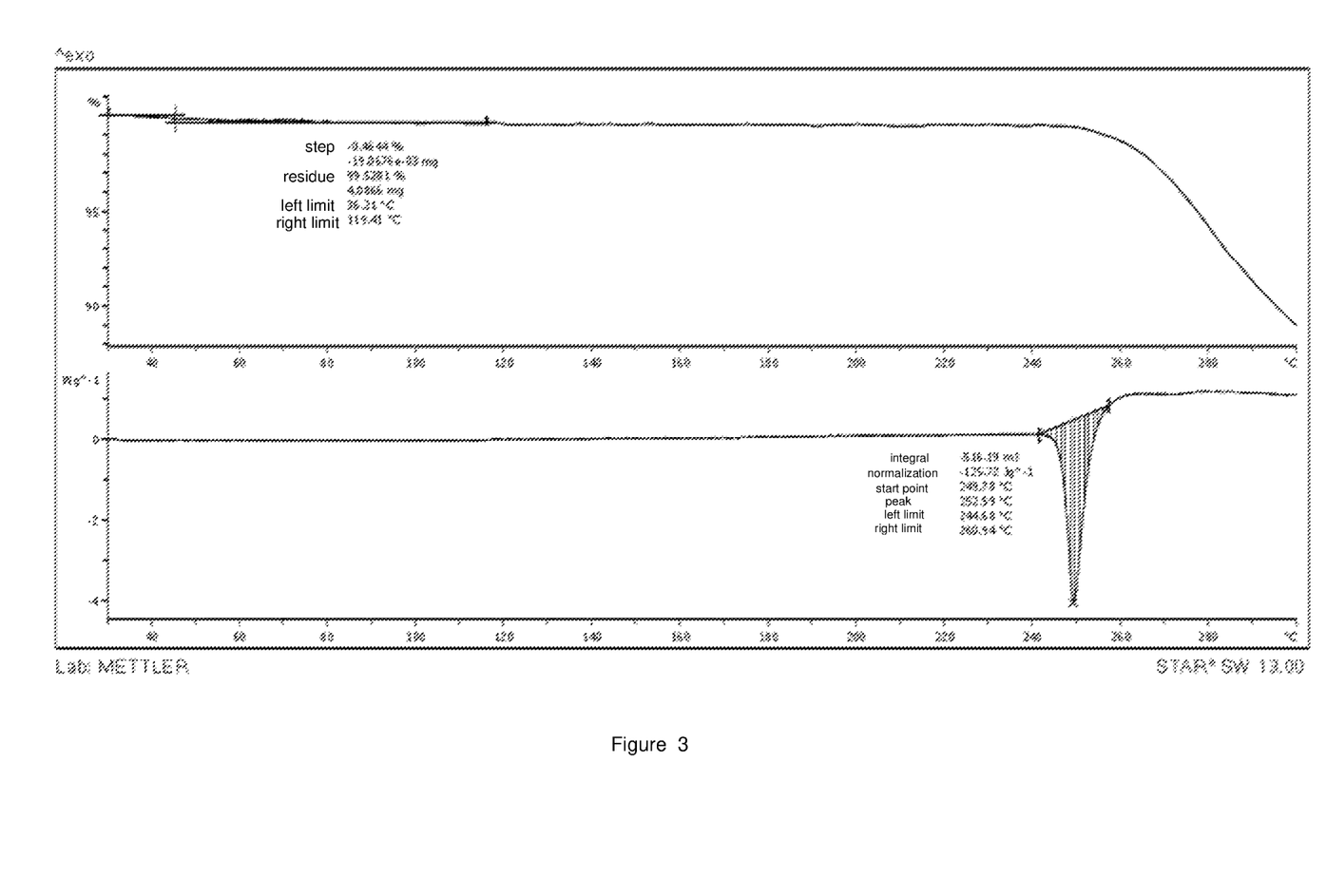
FIG. 3 is a DSC-TGA spectrum of the crystal form of deuterated AZD9291 mesylate provided in the present invention.

At the same time, we also carried out differential scanning calorimetry (DSC) and thermogravimetric analysis (TGA) on the crystal form of deuterated AZD9291 mesylate of the present invention, and the results are shown in FIG. 3. As can be seen from the DSC-TGA chart, the crystal form of the present invention has a low solvent residue and a high sample purity, which is ideal for subsequent pharmaceutical research.

Moreover, the deuterated AZD9291 mesylate crystal form of the present invention was used for oral bioavailability test in rats, and its oral bioavailability can reach 30.9%. The high bioavailability of oral administration proves that this crystal form is suitable for the development of oral preparations.

Figure 4:
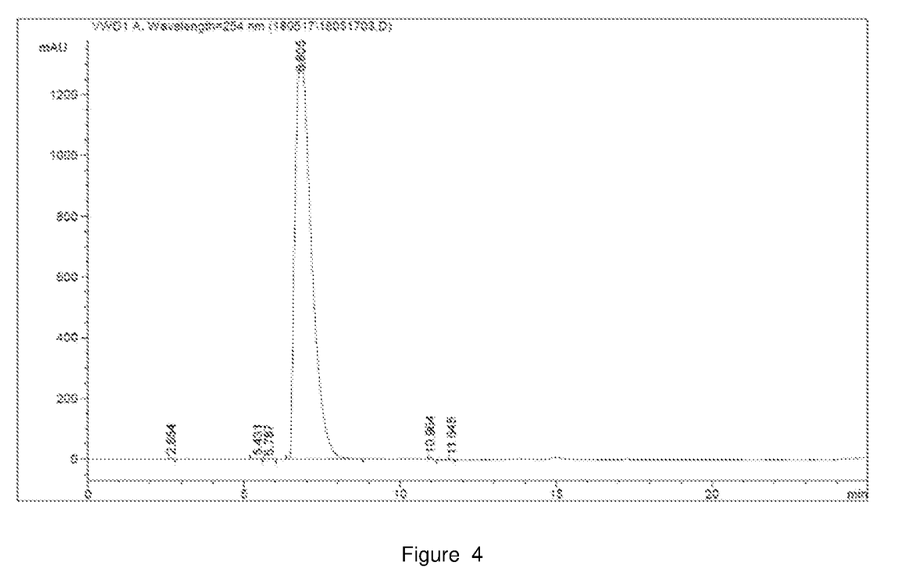
FIG. 4 is a liquid chromatogram of the crystal form of deuterated AZD9291 mesylate provided in the present invention.

The crystal form of the compound of the formula (I) or the formula (II) obtained by the method 1 or the method 2 of the present invention is not changed in moisture absorption or the like after being left at room temperature for 1 month. At the same time, through accelerated experiments, it was found that its physical and chemical properties were also stable. The crystal form was detected by HPLC (HPLC chart was shown in FIG. 4), and HPLC detection data was shown in Table 3. Its purity was as high as 99.83%, and the content of each single impurity was below 0.1%, which was suitable for the subsequent development of active pharmaceutical ingredient and preparations as well as subsequent pharmacokinetic experiments and zoological experiments.

TABLE 3

| No. | Retention time (min) | Peak area | Area percentage |
|---|---|---|---|
| 1 | 2.654 | 14.17814 | 0.0290 |
| 2 | 5.431 | 15.58395 | 0.0319 |
| 3 | 5.787 | 5.10229 | 0.0104 |
| 4 | 6.805 | 48830.4 | 99.8377 |
| 5 | 10.964 | 35.31213 | 0.0722 |
| 6 | 11.645 | 9.19170 | 0.0188 |
| total | | 48909.8 | 100.0000 |

The crystal form of deuterated AZD9291 mesylate prepared in the present invention was placed in a laboratory at room temperature, and the stability at room temperature was examined. The purity was measured by HPLC, and the results were shown in Table 4.

From the results in the table, the crystal form prepared in the present invention exhibits good stability at room temperature, and the purity is consistent according to HPLC detection.

TABLE 4

| lot number | Time (day) | character (visual inspection) | Purity (HPLC) |
|---|---|---|---|
| The deuterated AZD9291 mesylate crystal form prepared by method 2 of the present invention | 0 | off-white powder | 99.73% |
| | 15 | off-white powder (no hygroscopicity) | 99.70% |
| | 30 | off-white powder (no hygroscopicity) | 99.74% |

The crystal form of deuterated AZD9291 provided in the present invention can be used as an inhibitor of epidermal growth factor receptor EGFR, particularly an EGFR mutant inhibitor.

The crystal form of deuterated AZD9291 provided in the present invention can be used for the preparation of a medicament for modulating EGFR tyrosine kinase activity or treating EGFR-related diseases, which inhibits one or more EGFR activating or resistant mutations, such as L858R activating mutant, Exon19 deletion EGFR activating mutants, T790M resistant mutants, especially for cancer treatment, such as non-small cell lung cancer.

The invention claimed is:

1. A crystal form of deuterated AZD9291, characterized in that the structural formula is as shown in formula (I) or formula (II):

formula (I)

formula (II)

the X-ray powder diffraction of the crystal form obtained by Cu-Kα ray measurement has diffraction peaks at a 2θ angle (unit: °) of: 7.1±0.2, 8.5±0.2, 9.4±0.2, 10.3±0.2, 15.1±0.2, 16.3±0.2, 18.7±0.2, 22.0±0.2, 25.6±0.2, and 26.0±0.2.

2. A crystal form of deuterated AZD9291, characterized in that the structural formula is as shown in formula (I) or formula (II):

formula (I)

formula (II)

the X-ray powder diffraction of the crystal form obtained by Cu-Kα ray measurement has diffraction peaks at an 2θ angle (unit: °) of: 7.1±0.2, 8.5±0.2, 9.4±0.2, 10.3±0.2, 15.1±0.2, 16.3±0.2, 17.0±0.2, 17.3±0.2, 17.7±0.2, 18.7±0.2, 19.4±0.2, 19.7±0.2, 20.2±0.2, 20.7±0.2, 21.6±0.2, 22.0±0.2, 22.8±0.2, 23.5±0.2, 24.2±0.2, 24.8±0.2, 25.6±0.2, and 26.0±0.2.

3. A crystal form of deuterated AZD9291, characterized in that the structural formula is as shown in formula (I) or formula (II):

formula (I)

formula (II)

the X-ray powder diffraction obtained of the crystal form by Cu-Kα ray measurement has diffraction peaks at an 2θ angle (unit: °) of: 7.1±0.2, 8.5±0.2, 9.4±0.2, 10.3±0.2, 12.6±0.2, 14.4±0.2, 15.1±0.2, 15.6±0.2, 16.3±0.2, 17.0±0.2, 17.3±0.2, 17.7±0.2, 18.2±0.2, 18.7±0.2, 19.4±0.2, 19.7±0.2, 20.2±0.2, 20.7±0.2, 21.6±0.2, 22.0±0.2, 22.8±0.2, 23.5±0.2, 24.2±0.2, 24.8±0.2, 25.6±0.2, 26.0±0.2, 26.9±0.2, 27.7±0.2, 28.2±0.2, 29.5±0.2, 30.7±0.2, 31.7±0.2, 32.5±0.2, 33.1±0.2, 33.8±0.2, 34.6±0.2, 34.9±0.2, 35.6±0.2, 37.9±0.2, and 38.7±0.2.

4. A medicament comprising the crystal form of the deuterated AZD9291 according to claim 1.

5. A method of treating cancer comprising administering the crystal form of the deuterated AZD9291 according to claim 1, to a subject in need thereof, wherein the cancer is non-small cell lung cancer.

6. A method for preparing the crystal form of deuterated AZD9291 according to claim 1, comprising the following steps:
1) a deuterated AZD9291 compound is added to a solvent system, and heated to 40-80° C., and then methanesulfonic acid is added to the solvent system, wherein the mole number of methanesulfonic acid is 1 to 1.5 times of that of the deuterated AZD9291 compound, and maintained at 40 to 80° C. for 1 to 5 hours, and then hot-filtered;
2) the hot-filtered filtrate is allowed to be cooled at room temperature to precipitate crystals;
3) crystals are collected by filtration, washed and dried to obtain the crystal form of deuterated AZD9291 mesylate.

7. The method for preparing the crystal form according to claim 6, wherein the solvent system is any one of methanol, ethanol, isopropanol, acetone, acetonitrile, tetrahydrofuran, water, 1,4-dioxane, t-butyl acetate, an acetone/water mixture, an ethanol/t-butyl acetate mixture, and a 1,4-dioxane/water mixture.

8. The method for preparing the crystal form according to claim 7, wherein the solvent system is acetonitrile or an acetone/water mixture.

9. The method for preparing the crystal form according to claim 8, wherein the volume ratio of acetone to water in the acetone/water mixture is: acetone/water=10:1 to 15:1.

* * * * *